United States Patent [19]

Knifton et al.

[11] 4,366,259

[45] Dec. 28, 1982

[54] PRODUCTION OF ACETIC ACID AND PROPIONIC ACID AND THEIR ESTERS

[75] Inventors: John F. Knifton, Austin; Jiang-Jen Lin, Round Rock, both of Tex.

[73] Assignee: Texaco, Inc., White Plains, N.Y.

[21] Appl. No.: 316,195

[22] Filed: Oct. 29, 1981

[51] Int. Cl.³ .............................................. C07C 27/06
[52] U.S. Cl. .............................. 518/700; 252/431 N; 252/431 P; 518/715
[58] Field of Search ........................................ 518/700

[56] References Cited

U.S. PATENT DOCUMENTS

| | | | |
|---|---|---|---|
| 2,636,046 | 4/1953 | Gresham | 518/715 |
| 4,088,671 | 5/1978 | Kobylinski | 518/715 |
| 4,265,828 | 5/1981 | Knifton | 518/700 |
| 4,315,994 | 2/1982 | Knifton | 518/700 |

*Primary Examiner*—Howard T. Mars
*Attorney, Agent, or Firm*—Jack H. Park; Walter D. Hunter

[57] ABSTRACT

This invention concerns a process of making acetic acid and propionic acid and their esters which comprises contacting a mixture of CO and $H_2$ with a catalyst system comprising a ruthenium-containing compound and a cobalt halide dispersed in a low melting quaternary phosphonium or ammonium base or salt at a temperature of at least about 150° C. and at a pressure of about 500 psig or greater.

28 Claims, No Drawings

PRODUCTION OF ACETIC ACID AND PROPIONIC ACID AND THEIR ESTERS

BACKGROUND OF THE INVENTION

Field of the Invention

This invention concerns an improved process for preparing acetic acid and propionic acid and their esters by reaction of oxides of carbon with hydrogen in presence of a catalyst system.

There are ever-increasing efforts to provide new methods of making carboxylic acids such as acetic acid and esters thereof which are particularly useful in preparing a wide variety of organic compounds such as cellulose acetate, vinyl acetate etc. An ever present aim is to prepare such materials in relatively high yields directly from carbon monoxide and hydrogen utilizing a catalyst system providing good selectivity.

A number of processes have been described in the literature for manufacturing carboxylic acids and esters from carbon monoxide and alcohols or from carbon monoxide and hydrogen. For example, in U.S. Pat. No. 3,717,670 a method for preparing such carboxylic acids is disclosed in which an alcohol and carbon monoxide are reacted in the presence of a catalyst composition consisting of a rhodium compound and for example chromium trioxide. When hydrogen and carbon monoxide are passed over a catalyst comprising rhodium in combination with tungsten a reaction product containing acetic acid, acetaldehyde and/or ethanol is formed according to the disclosure of U.S. Pat. No. 4,096,164. A similar method is described in U.S. Pat. No. 4,014,913 where carbon monoxide and hydrogen are reacted in the presence of a rhodium-manganese catalyst. The reaction of carbon monoxide and hydrogen in the presence of a rhodium metal catalyst to give a liquid product containing a substantial proportion of acetic acid, ethanol and/or acetaldehyde is disclosed in U.S. Pat. No. 4,246,186. Likewise in U.S. Pat. No. 4,162,262 it is noted that the reaction of hydrogen and carbon monoxide in the presence of a catalyst comprising thorium and/or uranium yields a product containing a large amount of two-carbon atom products.

One of the problems associated with the above-described processes is that a wide variety of liquid organic products are formed also, generally the yield of carboxylic acids and esters is low. There is a definite need in the art therefore for a process which will give a high yield of the desired carboxylic acids and especially acetic acid and esters thereof.

SUMMARY OF THE INVENTION

This invention concerns a method for making acetic acid and propionic acid and their esters which comprises contacting a mixture of CO and $H_2$ with a catalyst system composed of a ruthenium-containing compound and a cobalt halide dispersed in a low melting quaternary phosphonium or ammonium base or salt at a temperature of at least about 150° C. and at a pressure of about 500 psi or greater.

DETAILED DESCRIPTION OF THE INVENTION

In the narrower and more preferred practice of this invention, acetic acid and propionic acid and their esters are prepared concurrently from a synthesis gas mixture of carbon monoxide and hydrogen by a one-step process comprising contacting said mixture of carbon monoxide and hydrogen with a catalyst system composed of a ruthenium-containing compound and a cobalt halide dispersed in a low melting quaternary phosphonium base or salt of an organic or mineral acid at a temperature of about 180° and about 250° C. and at a pressure of 2000 psig or greater.

The process of this invention is shown in the following equation where, for purposes of illustration, the reaction of carbon monoxide and hydrogen in the presence of the novel catalyst system yields acetic acid as follows:

$$2CO + 2H_2 \rightarrow CH_3COOH \qquad (1)$$

Although in the over-all reaction esters of acetic and/or propionic acid are also formed, the selectivity of the reaction to acetic acid is high and values in excess of 60% have been achieved.

The ruthenium-containing compound employed in the catalyst system of this invention as well as the cobalt halide may be chosen from a wide variety of organic or inorganic compounds, complexes, etc., as will be shown and illustrated below. It is only necessary that the catalyst system actually employed contain said metal in any of its ionic states. The actual catalytically active ruthenium species is then believed to comprise ruthenium in complex combination with carbon monoxide and hydrogen.

The ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) triiodide, tricarbonylruthenium(II) iodide, anhydrous ruthenium(III) chloride and ruthenium nitrate, or as the salt of a suitable organic carboxylic acid, for example, ruthenium(III) acetylacetonate. The ruthenium may also be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include oxides of ruthenium, ruthenium salts of a mineral acid, ruthenium salts of an organic carboxylic acid and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium(III) acetylacetonate, and triruthenium dodecacarbonyl. The usefulness of these ruthenium precursors, together with the cobalt halide in the catalyst system, for carboxylic acid and esters synthesis is illustrated by the accompanying examples.

Cobalt halides useful in the catalyst systems of this invention include cobalt(II) iodide, cobalt(II) bromide, cobalt(II) bromide hydrate, cobalt(II) chloride hydrate, anhydrous cobalt(II) chloride as well as mixtures thereof.

In a second embodiment of the process of this invention acetic acid and propionic acid and their esters are prepared by contacting a mixture of carbon monoxide and hydrogen at a pressure of about 500 psig or greater and a temperature of at least about 150° C. with a catalyst system comprising a ruthenium-containing compound of the type outlined above, a halogen-free cobalt compound plus, as a third component, an iodide or iodine compound dispersed in a low melting quaternary phosphonium or ammonium base or salt. In this case of catalysts, suitable halogen-free cobalt compounds may include cobalt oxides, for example, cobalt(II) oxide or cobalt(II,III) oxide, cobalt salts of mineral acids such as cobaltnitrate, hydrate, cobalt sulphate, etc., cobalt salts of organic carboxylic acids, for example, cobalt(II) formate, cobalt(II) acetate, cobalt(II) oxalate, cobalt naphthenate, as well as cobalt complexes with carbonyl-containing ligands as in the case of cobalt(III) acetylacetonate, etc. The cobalt may also be added as cobalt carbide, cobalt(II) carbonate and as a carbonyl or hydrocarbonyl derivative. Here suitable examples include dicobalt octacarbonyl, cobalt hydrocarbonyl and substituted cobalt carbonyl species thereof.

Suitable iodine in the practice of this invention include elemental iodine. Suitable iodide-containing compounds include ogranic iodides such as alkyl iodides, alkyal iodides and aryl iodides. Examples of suitable organic iodides are alkyl iodides such as methyl iodide, ethyl iodide etc.

Optionally in the first-described embodiment of the process of this invention an iodide or iodine compound of the kind illustrated above can be added to the catalyst combination previously outlined consisting of a ruthenium compound taken from the class described above and a halogen-containing cobalt compound also of the type previously described. The advantage of adding this third, iodine or iodide, component to the catalyst combination, consisting of a ruthenium-containing compound and a halogen-containing cobalt compound, is the improved selectivity to acetic acid that may be realized.

Generally, in the practice of this invention, the ruthenium-containing compound and the cobalt-containing compound, as well as the optional iodide or iodine-containing compound, are first dispersed in a low-melting quaternary phosphonium or ammonium salt a base, prior to their catalyst use is making carboxylic acids. It is interesting to note that the halogen-containing cobalt salt alone, when dispersed in the low-melting quaternary salt, has little, if any activity in promoting the manufacture of the desired acetic and propionic acids from synthesis gas.

The quaternary phosphonium or ammonium base or salt must be relatively low melting, that is, melt at a temperature less than the temperature of reaction. Usually the quaternary compound has a melting point less than about 180° C., and most often has a melting point less than 150° C.

Suitable quaternary phosphonium salts have the formula:

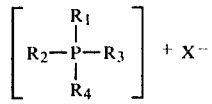

where $R_1$, $R_2$, $R_3$ and $R_4$ are organic radicals, particularly alkyl, aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, hydroxides, nitrates, chromates, tetrafluoroborates and other halides, such as the corresponding chlorides, are also satisfactory in this instance. Also useful are the corresponding quaternary ammonium bases and salts in the above series of compounds.

Equally useful are the phosphonium and ammonium salts containing phosphorus or nitrogen bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$-$C_{10}$ alkyl substituents, bonded to the phosphorus or nitrogen atom through the aryl function.

Illustrative examples of suitable quaternary phosphonium and ammonium bases and salts include tetrabutylphosphonium bromide, heptyltriphenylphosphonium bromide, tetrabutylphosphonium chloride, tetrabutylphosphonium nitrate, tetrabutylphosphonium hydroxide, tetrabutylphosphonium chromate, tetrabutylphosphonium tetrafluoroborate, tetrabutylphosphonium acetate, tetrabutyl ammonium bromide and tetramethyl-ammonium hydroxide, pentahydrate and trimethyldodecylammonium bromide.

The preferred quaternary salts are generally the tetralkylphosphonium salts containing alkyl groups having 1-6 carbon atoms, such as methyl, ethyl, and butyl. Tetrabutylphosphonium salts, such as tetrabutylphosphonium bromide, are most preferred for the practice of this invention.

Preferred tetrabutylphosphonium salts or bases include the bromide, chloride, acetate and chromate and hydroxide base.

Generally, in the catalyst system the molar ratio of the ruthenium compound to the quaternary phosphonium or ammonium salt or base will range from about 1:0.01 to about 1:100 or more and, preferably, will be from about 1:0.5 to about 1:20.

The quantity of ruthenium compound and the cobalt compound employed in the instant invention is not critical and may vary over a wide range. In general, the novel process is desirably conducted in the presence of a catalytically effective quantity of the active ruthenium species and of the cobalt species which gives the desired product in reasonable yield. The reaction proceeds when employing as little as about $1 \times 10^{-6}$ weight percent, and even lesser amounts, of ruthenium together with about $1 \times 10^{-6}$ weight percent or less of cobalt, basis the total weight of the reaction mixture. The upper concentration is dictated by a variety of factors including catalyst cost, the particular cobalt halide employed, partial pressures of carbon monoxide and hydrogen, operating temperature, etc. A ruthenium concentration of from about $1 \times 10^{-5}$ to about 5 weight percent in conjunction with a cobalt concentration of from about $1 \times 10^{-5}$ to about 5 weight percent, based on the total weight of reaction mixture is generally desirable in the practice of this invention. The preferred ruthenium-to-cobalt atomic ratio is from 10:1 to 1:10.

In these cases where the catalytic reaction mixture contains an iodine or iodide-containing compound, the synthesis of acetic and propionic acids from $Co/H_2$ may best be realized when the atomic ratio of total iodide in the system, as desired from the ruthenium-containing compound, the cobalt-containing compound, the low-melting quaternary phosphonium or ammonium salt and the optionally added iodine or iodide-containing compound, to the total cobalt content does not exceed about 6:1.

The temperature range which can usefully be employed in these synthesis is a variable dependent upon other experimental factors, including the pressure, and the concentration and choice of the particular species of ruthenium catalyst among other things. The range of operability is from about 150° to about 350° C. when superatmospheric pressure of syngas are employed. A narrow range of about 180° to about 250° C. represents the preferred temperature range. This narrower range is illustrated by the data in the accompanying Table 1.

Superatmospheric pressures of about 500 psig or greater lead to substantial yields of the carboxylic acids and by the process of this invention. A preferred operating range is from about 2000 psig to 10,000 psig, although pressures above 10,000 psig also provide useful yields of the carboxylic acids and their esters.

The relative amounts of carbon monoxide and hydrogen which may be initially present in the syngas mixture are variable, and these amounts may be varied over a wide range. In general, the mole ratio of $CO:H_2$ is in the range from about 20:1 up to about 1:20, preferable from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

The major by-products of the carboxylic acid process of this invention are most commonly the methyl, ethyl and propyl esters of acetic and propionic acids which are, of course, also useful compounds and major articles of commerce. The esters and the respective acids can easily be separated from one another by conventional means, e.g., fractional distillation in vacuo.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the carboxylic acids or ester products, and said materials as previously pointed out may be recovered by methods well known in the art, such as distillation, fractionation, extraction and the like. A fraction rich in ruthenium catalyst component and the cobalt halide may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analysis, or a combination of these techniques. Analysis have, for the most part, been by parts in weight; all temperatures are in degrees centigrade and all pressures in pounds per square inch gauge (psig).

The following examples illustrate various embodiments of this invention and are to be considered not limitive.

EXAMPLE I

A mixture of ruthenium (IV) oxide (4 mmoles) and cobalt iodide (8 mmoles) dispersed in tetrabutyl-phosphonium bromide (10.0 g) was transferred to a glass liner, under $N_2$ purge and charged to an 850 ml capacity pressure reactor equipped with heating and agitation means. The reactor was sealed, flushed with $CO/H_2$ and pressured to 2000 psig with 1:1 $CO/H_2$. The mixture is heated to 220° C. with rocking, the pressure raised to 7000 psig by $CO/H_2$ (1:1 molar) from a large surge tank, and the reactor held at temperature for 18 hr. Pressure in the reactor was maintained at about 7050 psig by incremental addition of the $CO/H_2$ mixture from the surge tank. On cooling, the reactor pressure (4150 psig) was noted, a typical gas sample taken and the excess gas removed. The emerald-green liquid product (16.4 g) showed no evidence of a solid fraction. Samples were analyzed by glc and Karl-Fischer titration and the following results were obtained:

63.8 wt.% acetic acid
12.1 wt.% propionic acid
10.1 wt.% ethyl acetate
7.1 wt.% ethyl propionate
3.5 wt.% propyl propionate.

Major product fractions are further identified by isolation and nmr, ir, etc.

Analysis of typical off-gas samples showed the presence of:

65.2% hydrogen
28.8% carbon monoxide
4.2% carbon dioxide
0.3% methane

Since the total catalyst charge to the glass liner was 13.3 g, the yield of liquid products was calculated to be:

$$\frac{16.4 - 13.8}{13.8} \times 100 = 24\%$$

Fractional distillation of a 5.8 g sample of the crude liquid product, under 0.5 mm Hg vacuum, produced a distillate sample comprising >80% acetic acid.

EXAMPLES 2–9

A number of additional examples were completed using the same procedures as in Example 1 and utilizing a number of different catalyst and low-melting quaternary salts combinations. Data relating to Examples 2–8 are included in Table I which follows.

It may be noted that a number of combinations of ruthenium compounds with cobalt halide salts and with different initial cobalt-to-ruthenium atomic ratios, when dispersed in tetrabutylphophonium halide salts, have been found to yield the desired carboxylic acids, e.g., acetic acid plus propionic acid.

TABLE I[a]

| Example | Catalyst | Melt | Pres. (psi) | Temp. (°C.) | HOAc | PrOOH | MeOAc | EtOAc + MeOOPr | PrOAc + EtOOPr | BuOOH + PrOOPr | H$_2$O | Liquid Yield % |
|---|---|---|---|---|---|---|---|---|---|---|---|---|
| 1 | RuO$_2$—2CoI$_2$ | Bu$_4$PBr | 7000 | 220 | 63.8 | 12.1 | 0.5 | 10.1 | 7.1 | 3.5 | 0.5 | 24 |
| 2 | RuO$_2$—CoI$_2$ | Bu$_4$PBr | 6900 | 220 | 26.5 | 10.5 | 4.3 | 21.9 | 17.3 | 7.4 | 1.4 | 172 |
| 3 | RuO$_2$—CoI$_2$ | Bu$_4$PBr | 6910 | 220 | 24.6 | 5.4 | 4.6 | 22.8 | 14.5 | 5.1 | 5.2 | 83 |
| 4 | RuO$_2$—½CoI$_2$ | Bu$_4$PBr | 7000 | 220 | 28.1 | 0.4 | 6.4 | 30.7 | 16.1 | 5.1 | 1.1 | 196 |
| 5 | Ru(acac)$_3$—CoI$_2$ | Bu$_4$PBr | 7000 | 220 | 61.2 | 10.0 | 2.0 | 9.9 | 8.5 | 2.1 | 0.5 | 88 |
| 6 | Ru$_3$(CO)$_{12}$—CoI$_2$ | Bu$_4$PBr | 7000 | 220 | 48.5 | 24.1 | 0.9 | 9.8 | 7.4 | 3.9 | 0.6 | 88 |
| 7 | RuO$_2$—CoBr$_2$ | Bu$_4$PBr | 6730 | 220 | 22.3 | 0.9 | 2.0 | 18.3 | 8.2 | 2.2 | 11.4 | 105 |
| 8 | RuO$_2$—CoCl$_2$ | Bu$_4$PBr | 7000 | 220 | 3.4 | — | 13.0 | 34.0 | 15.2 | 4.1 | 2.5 | 392 |
| 9 | RuO$_2$—CoCl$_2$ | Bu$_4$PCl | 7000 | 220 | 5.1 | 2.3 | 21.8 | 37.3 | 4.8 | 2.2 | 3.7 | 321 |

[a] Charge: Ruthenium, 4.0 mmole; tetrabutylphosphonium salt, 10 g; Run Conditions: 1:1 molar (CO/H$_2$), 18 hrs.
[b] Designations: Acetic Acid (HOAC); Propionic Acid (PrOOH); Butyric Acid (BuOOH), Acetate Esters (MeOAc, EtOAc, PrOAc); Propionate Esters (MeOOPr, EtOOPr, PrOOPr).
[c] Variable pressure run, 4000 psi CO/H$_2$ initial.

EXAMPLE 10

This example illustrates a further synthesis of acetic acid in high yield together with propionic acid and their esters directly from synthesis gas using a cobalt-ruthenium containing catalyst dispersed in tetrabutylphosphonium bromide salt (m.p. 100° C.).

A mixture of ruthenium(IV) oxide (4 mmoles) and cobalt(II) iodide (4 mmoles) dispersed in tetrabutylphosphonium bromide (10.0 g) was charged to a glass liner, under nitrogen purge, and transferred to a 450 ml capacity pressure reactor equipped with heating and means of agitation. The reactor was sealed, flushed with CO/H$_2$ mixture and pressured to 4000 psig. with a 1:2 molar CO/H$_2$ mixture. The mixture was heated to 220° C. with rocking, the pressure allowed to rise to ca. 7200 psig., and the reactor held at temperature for 18 hours.

On cooling, the reactor pressure (3530 psig.) was noted, a typical gas sample taken and the excess gas removed. A dark green liquid product (16.9 g) was recovered and samples were analyzed by glc and Karl-Fischer titration and following results were obtained:

70.4 wt.% acetic acid
6.9 wt.% propionic acid
1.5 wt.% ethyl acetate
7.5 wt.% propyl acetate
0.5 wt.% water Analysis of typical off-gas samples showed the presence of:

25% hydrogen
67% carbon monoxide
5.9% carbon dioxide
0.7% methane

Since the total catalyst charge to the glass liner was 12.0 g, the yield of liquid organics was calculated to be 41%.

Fractional distillation of a 12.1 g sample of the crude liquid product, under 0.05 mm Hg vacuum, produced a distillate fraction comprising >80% acetic acid.

EXAMPLES 11–14

Following the general procedure of Example 1, for additional examples were completed utilizing different ruthenium-cobalt catalyst combinations in tetrabutylphosphonium bromide. Data relating to Examples 11–14 are included in Table II which follows.

It may be noted that:

(a) for the ruthenium(IV) oxide-cobalt(II) iodide combination dispersed in tetrabutylphosphonium bromide, the addition of elemental iodine to the reaction mixture results in informal selectivity to acetic acid in the liquid product (see Examples 2, 11 and 12).

(b) Acetic acid and propionic acid may be prepared directly from carbon monoxide and hydrogen using as a catalyst a ruthenium compound in combination with a halide-free cobalt compound plus a source of iodine. In these cases, acetic acid formation is illustrated for the ruthenium(IV) oxide-cobalt(III) acetylacetonate-iodine and ruthenium(IV) oxide-dicobalt octacarbonyl-iodine combinations (see Example 13 and 14).

TABLE II[a]

| Example | Catalyst | Melt | Pres. (psi) | Temp. (°C.) | HOAc | PrOOH | MeOAc | EtOAc + MeOOPr | PrOAc + EtOOPr | BuOOH + PrOOPr | H$_2$O | Liquid Yield % |
|---|---|---|---|---|---|---|---|---|---|---|---|---|
| 2 | RuO$_2$—CoI$_2$ | Bu$_4$PBr | 6900 | 220 | 26.5 | 10.5 | 4.3 | 21.9 | 17.3 | 7.4 | 1.4 | 172 |
| 11 | RuO$_2$—CoI$_2$—½I$_2$ | Bu$_4$PBr | 7000 | 220 | 62.7 | 22.7 | 0.4 | 4.0 | 3.2 | 1.8 | 0.7 | 59 |
| 12 | RuO$_2$—CoI$_2$—I$_2$ | Bu$_4$PBr | 7000 | 220 | 86.3 | — | — | 6.3 | 2.1 | — | — | 59 |
| 13 | RuO$_2$—Co(acac)$_3$—I$_2$ | Bu$_4$PBr | 7000 | 220 | 36.6 | 12.0 | 2.9 | 18.8 | 11.5 | 4.7 | 1.1 | 105 |
| 14 | RuO$_2$—½Co$_2$(CO)$_8$—I$_2$ | Bu$_4$PBr | 7000 | 220 | 28.1 | 5.6 | 4.4 | 23.6 | 16.8 | 8.0 | 1.2 | 114 |

[a] Charge: Ruthenium, 4.0 mmole; Tetrabutylphosphonium Bromide, 10 g; Run Conditions: 1:1 molar (CO/H$_2$); 18 hrs.
[b] Designations as Per Table I.

COMPARATIVE EXAMPLE 15

In this comparative example, the catalyst utilized consisted only of the halide-containing cobalt compound dispersed in the low-melting quaternary salt. There was no ruthenium catalyst component in this example. No acetic or propionic acids were formed in the absence of the ruthenium component.

Cobalt iodide (8 mmoles) dispersed in tetra butylphosphonium bromide (10.0 g) was transferred to a glass liner, under N$_2$ purge and charged to an 850 ml capacity pressure reactor equipped with heating and agitation means. The reactor was sealed, flushed with CO/H$_2$ and pressured to 2000 psig with 1:1 molar CO/H$_2$. The mixture was heated to 220° C. with rocking, the pressure raised to 7000 psig by CO/H$_2$ (1:1 molar) from a large surge tank, and the reactor held at temperature for 18 hr. Pressure in the reactor was maintained at about 7050 psig by incremental addition of the CO/H$_2$ mixture from the surge tank. On cooling, the reactor pressure was released; the product within the glass liner consisted of 12.5 g of deep-blue liquid material. Samples of this liquid which were analyzed by glc showed no evidence for the presence of acetic or propionic acids. The yield of liquid product was calculated to be <2%.

EXAMPLE 16

A mixture of ruthenium(III) acetylacetonate (2 mmoles) and cobalt iodide (2 mmoles) dispersed in tetrabutylphosphonium bromide (10.0 g) was transferred to a glass liner, under N$_2$ purge and charged to an 850 ml capacity pressure reactor equipped with heating and agitation means. The reactor was sealed, flushed with CO/H$_2$ and pressured to 2000 psig with 1:1 molar CO/H$_2$. The mixture was heated to 220° C. with rocking, the pressure raised to 7000 psig by CO/H$_2$ (1:1 molar) from a large surge tank, and the reactor held at temperature for 18 hr. Pressure in the reactor was maintained at about 6950 psig by incremental addition of the CO/H$_2$ mixture from the surge tank. On cooling, the reactor pressure (4000 psig) was noted, a typical gas sample taken and the excess gas removed. The emerald-green liquid product (20.6 g) showed no evidence of a solid fraction. Samples were analyzed by glc and Karl-Fischer titration and the following results were obtained:

59.8 wt.% acetic acid
11.7 wt.% propionic acid
9.6 wt.% ethyl acetate
7.5 wt.% ethyl propionate
1.5 wt.% propyl propionate Major product fractions were further identified by isolation and nmr, ir, etc. The liquid yield was estimated to be 81%.

The crude product liquid after analysis was subject to distillation, in vacuo, and the acetic acid and, propionic acid plus their esters isolated as distillate fractions. The residual ruthenium-cobalt catalyst (8.9 g) was returned to the glass lined reactor, the reactor sealed, flushed with CO/H$_2$, and pressured to 2000 psig with 1:1 molar CO/H$_2$. The mixture was heated to 220° C. with rocking, the pressure raised to 7000 psig by CO/H$_2$ (1:1 molar) from a large surge tank, and the reactor held at temperature for 18 hr. In this manner the synthesis of acetic plus propionic acids is repeated, and the later are again recovered from the iodide liquid product (15.2 g) by fractional distillation in vacuo. The CO-hydrogenation to acetic and propionic acids was repeated using the same ruthenium-cobalt catalyst sample an additional two times. After each cycle the crude liquid products were subject to analysis. The results for the four catalyst cycle experiment are summarized in Table III, below.

TABLE III[a]

| Ruthenium-Cobalt Catalyst Cycle | Liquid Product Composition (wt. %)[b] | | | | | Liquid Yield (%) |
|---|---|---|---|---|---|---|
| | HOAc | PrOOH | EtOAc MeOOPr | PrOAc EtOOPr | BuOOH PrOOPr | |
| I | 59.8 | 11.7 | 9.6 | 7.5 | 1.5 | 81 |
| II | 65.8 | 5.5 | 9.5 | 2.0 | — | 88 |
| III | 61.5 | 10.1 | 10.6 | 8.3 | 1.8 | 90 |
| IV | 56.0 | 4.6 | 18.3 | 10.5 | 2.0 | 33 |

[a]Charge: Ru(acac)$_3$, 2.0 mmole; CoI$_2$, 2.0 mmole; Bu$_4$PBr, 10 g; Run Conditions: 7000 psig; 220C; CO/H$_2$ (1:1 molar), 18 hr.
[b]Designations as Per Table I.

It is claimed:

1. A process for making acetic acid and propionic acid and their esters that comprises contacting a mixture of CO and H$_2$ with a catalyst system comprising a ruthenium-containing compound and a cobalt halide selected from the group consisting of cobalt(II) chloride, cobalt(II) bromide and cobalt(II) iodide dispersed in a low melting quaternary phosphonium or ammonium base or salt at a pressure of about 500 psig or greater and at a temperature of at least about 150° C. for a sufficient time to provide said carboxylic acids and their esters.

2. The process of claim 1 wherein the process is conducted at a temperature of about 150° to about 350° C.

3. The process of claim 1 wherein the said process is conducted at a pressure of about 2000 to about 10,000 psig.

4. The process of claim 1 wherein said quaternary salt or base has a melting point less than about 180° C.

5. The process of claim 1 wherein said quaternary salt is a tetraalkylphosphonium salt.

6. The process of claim 5 wherein said alkyl groups contain 1–6 carbon atoms.

7. The process of claim 1 wherein said quaternary is a mixed alkylaryl phosphonium quaternary.

8. The process of claim 1 wherein said quaternary salt is tetrabutylphosphonium salt.

9. The process of claim 7 wherein said tetrabutylphosphonium salt is selected from the group consisting of tetrabutylphosphonium bromide, tetrabutylphosphonium chloride, tetrabutylphosphonium acetate and tetrabutylphosphonium chromate.

10. The process of claim 1 wherein the said quaternary salt is tetrabutylphosphonium bromide.

11. The process of claim 1 wherein the ruthenium-containing compound is selected from the group consisting of one or more oxides of ruthenium, ruthenium salts of a mineral acid, ruthenium salts of an organic carboxylic acid and ruthenium carbonyl or hydrocarbonyl derivatives.

12. The process of claim 1 wherein the ruthenium-containing compound is selected from the group consisting of anhydrous ruthenium(IV) dioxide, ruthenium(IV) dioxide hydrate, ruthenium(VIII) tetraoxide, ruthenium(III) trichloride hydrate, ruthenium acetate, ruthenium propionate, ruthenium(III) acetylacetonate and triruthenium dodecarbonyl.

13. The process of claim 1 wherein said ruthenium-containing compound is ruthenium(IV) dioxide.

14. The process of claim 1 wherein said ruthenium-containing compound is ruthenium(III) acetylacetonate.

15. The process of claim 1 wherein said ruthenium-containing compound is triruthenium dodecacarbonyl.

16. The process of claim 1 wherein the said cobalt halide is cobalt(II) iodide.

17. The process of claim 1 wherein the said cobalt halide is cobalt(II) bromide.

18. The process of claim 1 wherein the catalyst system also contains an iodide or iodine containing compound.

19. The process of claim 18 wherein the iodine-containing compound is elemental iodine.

20. The process of claim 18 wherein the iodide-containing compound is an alkyl iodide.

21. The process of claim 20 wherein the alkyl iodide is methyl iodide.

22. A process for making acetic and propionic acids and their esters which comprises contacting a mixture of CO and $H_2$ at a pressure of about 500 psig or greater and at a temperature of at least about 150° C. with a catalyst system comprising a ruthenium-containing compound a halogen-free cobalt compound and an iodide or iodine-containing compound dispersed in a low-melting quaternary phosphonium or ammonium base or salt.

23. The process of claim 22 wherein said cobalt compound is selected from the group consisting of cobalt(III) acetylacetonate and dicobalt octacarbonyl.

24. The process of claim 22 wherein the said catalyst system contains an iodine-containing compound.

25. The process of claim 24 wherein the said iodine-containing compound is elemental iodine.

26. The process of claim 22 wherein the said catalyst system contains an iodide compound.

27. The process of claim 26 wherein the said iodide compound is an alkyl iodide.

28. The process of claim 27 wherein the said iodide compound is methyl iodide.

* * * * *